Figure 1:
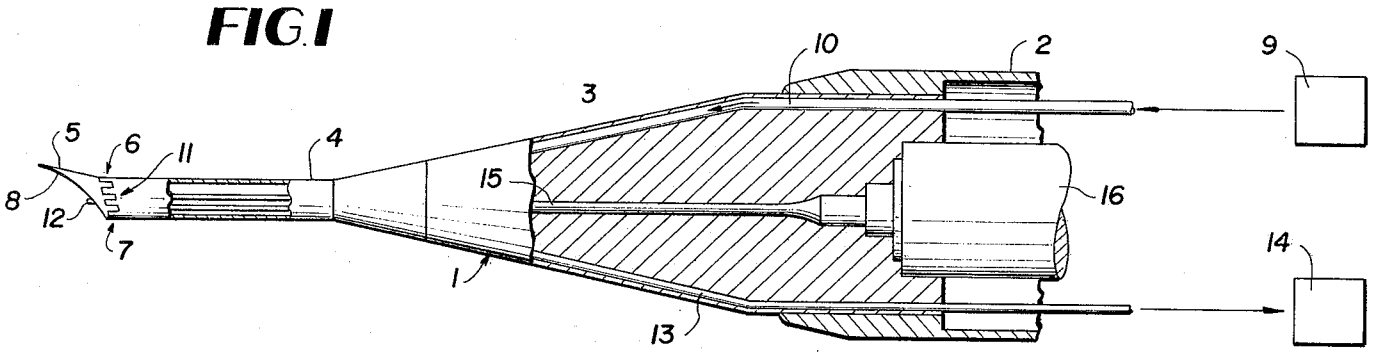
Figure 2:
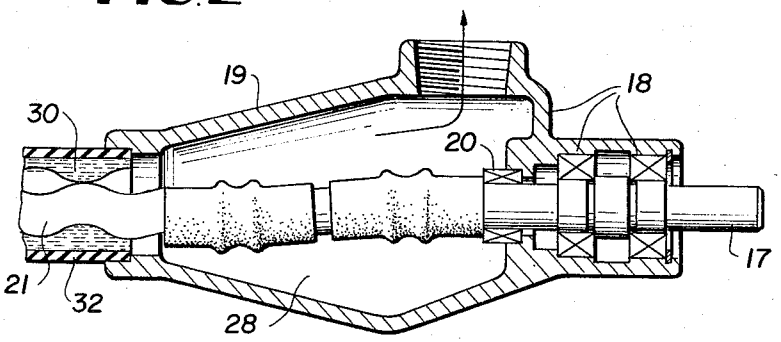
Figure 3A:
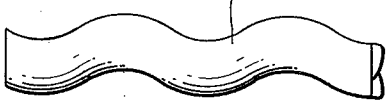
Figure 3B:
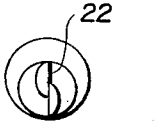
Figure 4A:
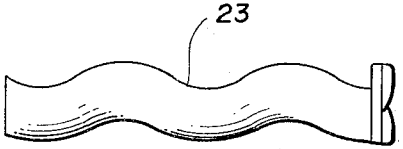
Figure 4B:
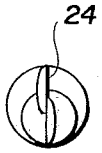
Figure 5A:
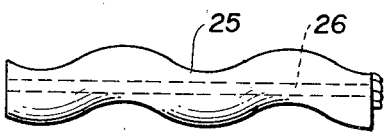
Figure 5B:
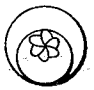

United States Defensive Publication [19] (H) [11] T102,001

Ballintine [43] Jul. 6, 1982

[54] DEVICE FOR EXTRACTION OF CATARACTS USING MINIATURIZED PROGRESSING CAVITY PUMP

[76] Inventor: Elmer J. Ballintine, 9203 Cedarcrest St., Bethesda, Md. 20014

[21] Appl. No.: 270,657

[22] Filed: Jun. 4, 1981

[51] Int. Cl.[3] ..... A61M 1/00

[52] U.S. Cl. ..... 128/276; 128/305

[57] ABSTRACT

A surgical tissue macerating and removal instrument or tool having a rotating, longitudinally progressing rotor member in a miniaturized Moyno pump cavity, disposed within a hypodermic tube, which itself is coaxially disposed in an extension of a tool handle. A frusto-conical member extends into the tool handle extension and is provided with a cut-off tissue engaging edge at the end distant from the tube. The pump rotor is provided at the end distant from the tube with a cutting edge or other means suitable for drilling into the cataractous lens of an eye. Apertures are provided in the extension adjacent the frusto-conical member so that a treatment fluid may be supplied in the annular space between the tube and the extension and thus may flow to the aperture site. An aperture is provided in the frusto-conical member between the extension and the tube so that the treatment fluid may also enter into the tube where it mixes with macerated tissue being directed through an aperture in the tube to a passageway which may have suction applied thereto to help remove macerated material from the operative site. Radially-inwardly extending fins may be provided on the interior surface of the frusto-conical member to inhibit or prevent rotation of the cataractous lens tissue being macerated.

1 Claim, 1 Sheet Drawing,

11 Pages Specification

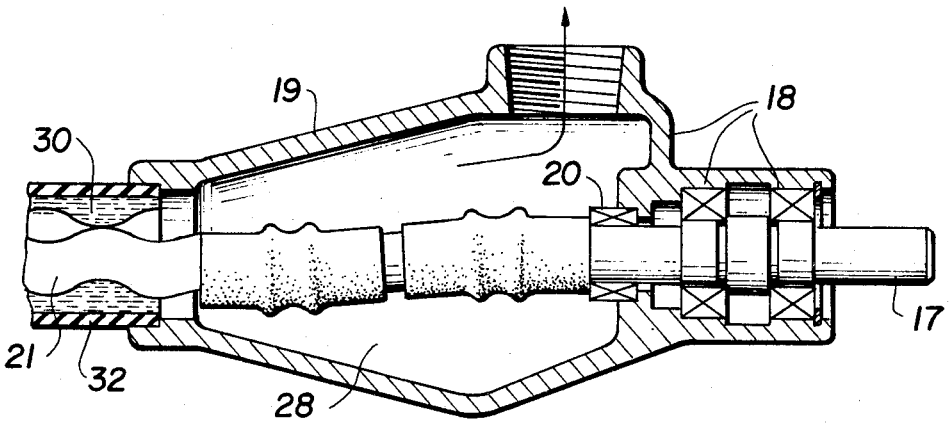

The file of this unexamined application may be inspected and copies thereof may be purchased (849 O.G. 1221, Apr. 9, 1968).